United States Patent [19]
Palumbo

[11] Patent Number: 5,613,943
[45] Date of Patent: Mar. 25, 1997

[54] DYNAMIC PATELLA BRACE WITH FLOATING PATELLA PAD

[75] Inventor: Pasquale M. Palumbo, McLean, Va.

[73] Assignee: Dynorthotics LP, Vienna, Va.

[21] Appl. No.: 378,606

[22] Filed: Jan. 26, 1995

[51] Int. Cl.⁶ .................................................... A61F 5/00
[52] U.S. Cl. ............................................. 602/62; 602/26
[58] Field of Search ................................ 602/20, 23, 26, 602/61, 62; 2/24, 62; 128/892

[56] References Cited

U.S. PATENT DOCUMENTS

| | | |
|---|---|---|
| D. 307,054 | 4/1990 | Johnson . |
| 3,318,305 | 5/1967 | Schultz ........................................ 602/26 |
| 3,473,527 | 10/1969 | Spiro ............................................ 602/26 |
| 3,804,084 | 4/1974 | Lehman ....................................... 602/26 |
| 4,084,584 | 4/1978 | Detty . |
| 4,201,203 | 5/1980 | Applegate .................................. 602/26 |
| 4,287,885 | 9/1981 | Applegate .................................. 602/26 |
| 4,296,744 | 10/1981 | Palumbo ..................................... 602/26 |
| 4,353,362 | 10/1982 | DeMarco . |
| 4,370,978 | 1/1983 | Palumbo . |
| 4,372,298 | 2/1983 | Lerman ...................................... 602/26 |
| 4,407,276 | 10/1983 | Bledsoe . |
| 4,423,720 | 1/1984 | Meier et al. . |
| 4,425,912 | 1/1984 | Harper . |
| 4,445,505 | 5/1984 | Labour et al. . |
| 4,466,428 | 8/1984 | McCoy . |
| 4,492,227 | 1/1985 | Senn et al. . |
| 4,495,942 | 1/1985 | Palumbo . |
| 4,532,921 | 8/1985 | von Torklus et al. . |
| 4,607,628 | 8/1986 | Dashefsky . |
| 4,685,153 | 8/1987 | Sims . |
| 4,941,462 | 7/1990 | Lindberg . |
| 5,016,621 | 5/1991 | Bender . |
| 5,024,216 | 6/1991 | Shiono ........................................ 602/26 |
| 5,085,210 | 2/1992 | Smith, III . |
| 5,086,761 | 2/1992 | Ingram . |
| 5,139,015 | 8/1992 | Morneau . |
| 5,139,476 | 8/1992 | Peters . |
| 5,139,477 | 8/1992 | Peters . |
| 5,156,163 | 10/1992 | Watkins et al. . |
| 5,168,577 | 12/1992 | Detty ........................................... 602/26 |
| 5,181,906 | 1/1993 | Bauerfeind . |
| 5,221,252 | 6/1993 | Caprio, Jr. et al. . |
| 5,277,697 | 1/1994 | France et al. . |

*Primary Examiner*—Richard J. Apley
*Assistant Examiner*—Kim M. Lee
*Attorney, Agent, or Firm*—Jim Zegeer, Esq.

[57] ABSTRACT

A dynamic patella brace useful for both diagnosis and treatment of patella subluxation, wherein the position of a patella bracing pad is allowed to float to be automatically dynamically repositionable depending upon the amount of flexion and movement of the knee and the amount of tension and pressure applied is provided. The brace includes an elastic sleeve having an aperture for registration and alignment of the knee therein. Additionally, the brace includes a strap assembly to which a plurality of elastic arm members and a patella bracing pad are attached. The strap also includes an anchor which serves to isolate the patella bracing pad from a counterarm member to allow the dynamic repositioning of the pad when the knee is flexed. The patella brace may be used to facilitate positive diagnosis of patella subluxation whose symptoms may mimic other pathological problems of the knee, and, therefore, lead to an erroneous diagnosis. The brace may also be used for treatment and/or to delay or avoid the need for corrective surgery.

31 Claims, 2 Drawing Sheets

DYNAMIC PATELLA BRACE WITH FLOATING PATELLA PAD

FIELD OF THE INVENTION

The present invention relates to knee support devices, and more particularly dynamic patella brace for stabilizing the patella to prevent patella subluxation, chondromalacia and other symptomatic conditions of the extensor mechanism during all normal degrees of knee flexion and extension, utilizing a patella pad retainer which allows the pad to float and be dynamically repositioned with the knee movement.

BACKGROUND OF THE INVENTION

It is well known that loosely ligamented individuals, as well as individuals with certain peculiar anatomic features of certain components of the knee, frequently develop various pathological problems with their knees, particularly when these individuals are active in physically strenuous activities, such as, for example, athletics. The most commonly occurring problems relate to stretching or tearing of various knee ligaments, injury to the cartilage (meniscal) and articular surfaces of the knee joint, and fractures. Patella subluxation, or abnormal and undesirable movement of the patella, laterally, relative to its normal up-and-down movement in the vertical track defined by the trochlea, can precipitate the onset of chondromalacia or aggravate existing chondromalacia of the patella, as well as cause diagnostic problems and other painful clinical conditions with respect to the knee.

Subluxation of the patella can be caused by certain developmental abnormalities of the skeletal components of the knee and/or the presence of musculoligamentous laxity, or dysplasia. The patella may leave its normal vertical tracking groove as a result of abnormal vector forces and/or by passive lateral or rotary forces. The abrupt abnormal lateral displacement of the patella from its groove during any weight-bearing activity, such as, for example, running, stair climbing, etc., frequently results in an immediate, temporary disability, such as, for example, buckling of the knee, thereby causing a subjective sensation in the knee similar to that caused by other unrelated pathological conditions within the knee.

The sensation of pain and/or imminent buckling of the knee results in apprehension and restriction of certain weight-bearing activities, such as, for example, athletic endeavors. The resultant increased abnormal traction forces on the peripatellar soft tissues frequently lead to inflammatory changes and stretching of the retinaculae, patella ligament and/or tendon (tendinitis).

Furthermore, the repetitive, abnormal lateral excursions, which cause abnormal shearing forces, frequently lead to early, accelerated and progressive degenerative changes (chondromalacia) of the patella and femoral condyles.

As noted above, problems peculiar to the patella comprise only a portion of all common physiological problems of the knee, and several, unrelated or partially related problems may occur simultaneously, particularly in individuals having loose ligaments, or when engaged in relatively strenuous activities involving the knee.

Young children still in the active bone-growth phase of life frequently are relatively loosely ligamented and suffer from various degrees of patella subluxation. It is well recognized that it is preferable to avoid or delay corrective surgery for such individuals, if at all possible, until such individuals reach a more physiologically opportune age, i.e., when their growth plates have closed.

Others have devoted attention and proposed various knee braces and supports directed to general problems of the knee. Examples of such patents are U.S. Pat. No. 3,473,527 to Spiro; U.S. Pat. No. 3,804,084 to Lehman; U.S. Pat. No. 3,853,123 to Moore; and U.S. Pat. No. 4,532,921 to von Torklus et al., which have proposed various knee-support, brace and knee-splinting devices intended to restrain the knee to prevent normal knee flexion or movement. These are but a few of the patents directed to knee supports.

U.S. Pat. No. 3,926,186 to Nirschl and U.S. Pat. No. 3,945,046 to Stromgern propose other muscular and flexible knee supports. Nirschl's apparatus, however, is not designed to provide medial-lateral stabilization of the patella, and is inherently incapable of performing a dynamic bracing function for the patella. Stromgern's apparatus, on the other hand, is not concerned with patella stabilization, but, instead, is directed to the general problem of providing stability to the medial knee ligament complex.

U.S. Pat. No. 4,084,585 to Detty discloses a simple knee sleeve device which includes a pad but which is capable of providing limited, static patella bracing when the knee is passive, i.e., not in motion or when in a single position or a narrow range of positions.

Perhaps the seminal patent for providing dynamic patella bracing is U.S. Pat. No. 4,296,744 to Palumbo, the inventor of the present invention, which discloses a dynamic patella brace that applies medial pressure to the patella throughout substantially the complete physiologic range of flexion and movement of the knee when the brace is in use. Even this patent, whose principles have been widely accepted over the years, suffers from the disadvantage that when the brace is in use, the patella bracing pad tends to be maintained in a relatively rigidly fixed position during flexion of the knee, and thus fails to effectively maintain pressure on the patella during flexion. This rigidity in the positioning of the pad results in lowered efficacy of the brace, because the pad is not permitted to dynamically reposition itself with respect to the sleeve or to float with respect to the patella during flexion of the knee, and thus the pad does not remain as effectively positioned as when the brace was initially engaged.

SUMMARY OF THE INVENTION

The present invention provides an improved dynamic patella brace that overcomes deficiencies of known patella bracing systems and is an improvement over my prior invention described in U.S. Pat. No. 4,296,744. In particular, the present invention provides a dynamic patella brace wherein the patella bracing pad is allowed to float so as to maintain its most effective operative position with respect to the patella when the knee is flexed.

It is an object of the invention to provide an improved dynamic patella brace wherein the patella bracing pad dynamically floats when the knee is flexed.

Another object of the invention is to provide an improved dynamic patella brace that maintains a patella bracing pad in the most effective position with respect to the patella during flexion of the knee.

Another object of the present invention is to provide an improved dynamic patella brace having a patella bracing pad adapted to float and closely follow the movement of the patella.

Still another object of the present invention is to provide an improved dynamic patella brace useful for both diagnosis and treatment of patella subluxation.

A further object of the present invention is to provide an improved dynamic patella brace for alleviating certain physiological problems of the knee related to, or aggravated by, patella subluxation.

Yet another object of the present invention is to provide an improved dynamic patella brace capable of performing its bracing or splinting function for the patella during the full, or normal, range of knee flexion and movement.

A still further object of the invention is to provide an improved dynamic patella brace to facilitate proper and positive diagnosis of patella subluxation, particularly in its milder form when its clinical presentation simulates that of other pathological conditions of the knee.

Another object of the present invention is to provide an improved dynamic patella brace suitable for use in children having patella subluxation, but whose growth plates are still open, so as to delay or avoid the need for corrective surgery until a more physiologically opportune time is reached.

A still further object is to provide an improved dynamic patella brace offering other treatment advantages and for treating painful conditions of the extensor mechanism.

A further object of the invention is to provide an improved patella brace which is relatively simple to put in place and which will provide dynamic patella bracing without the need for constant adjustment or readjustment.

Yet another object of the invention is to provide an improved dynamic patella brace which can be utilized with minimal discomfort without being unsightly and without requiring the user to utilize crutches or to walk in an unnatural manner.

Another object of the present invention is to provide an improved dynamic patella brace having a relatively simple construction, which is relatively simple to manufacture.

These and other objects, and their attendant advantages, are achieved by the present invention, which provides an improved dynamic patella brace comprising: a patella bracing strap including an anchor, a patella bracing pad and first and second arm members extending therefrom, the first ends of which are adapted to be wrapped about the knee of a user to apply a dynamic resultant force in the medial direction to the patella, via the patella bracing pad, throughout substantially the complete physiologic range of flexion and movement of the knee when the brace is in use; the anchor member, arranged to be disposed laterally adjacent the patella bracing pad so as to maintain the patella bracing pad positioned laterally adjacent to the patella throughout the complete functional physiologic range of motion and movement of the knee; an intermediate elastic member adapted to be disposed between the anchor and the patella bracing pad to allow the patella bracing pad to float with the movement of the knee and to be dynamically repositioned depending upon the amount of flexion and movement of the knee when the brace is in use; and an elastomeric sleeve having an aperture for receiving the patella of the user and adapted to have the knee positioned substantially therein enables the anchor to be fastened thereto in a predetermined location when the brace is in use.

BRIEF DESCRIPTION OF THE DRAWINGS

The invention will be described in detail herein with reference to the following drawings in which like reference numerals refer to like elements throughout the several views, and wherein.

DETAILED DESCRIPTION OF PREFERRED EMBODIMENTS

Figure 1:
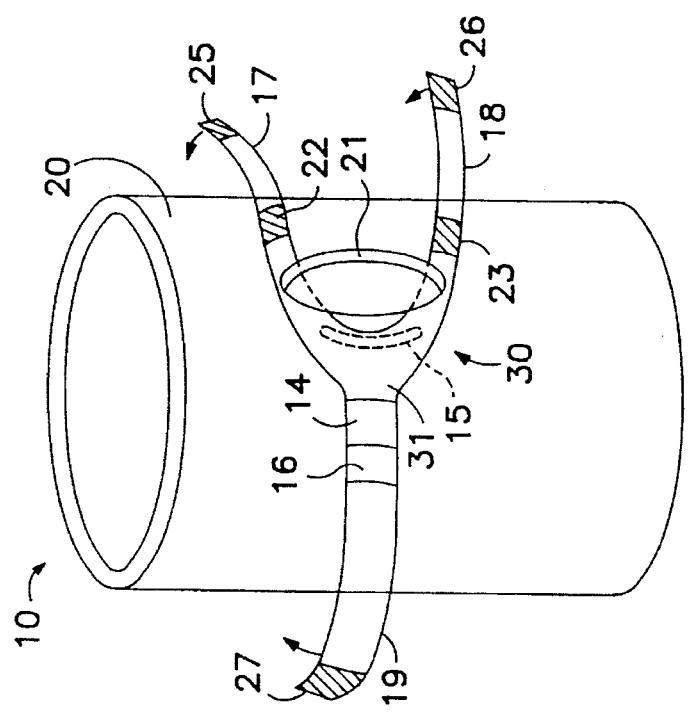
FIG. 1 is a perspective view of the dynamic patella brace according to one embodiment of the present invention.
Figure 3:
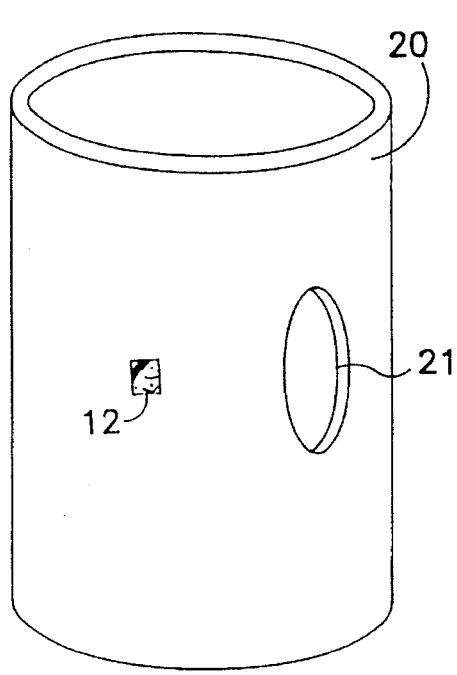
FIG. 3 is a perspective view of the elastomeric sleeve of the dynamic patella brace prior to the attachment of the strap assembly thereto.

FIG. 1 shows a perspective view of an embodiment of the dynamic patella brace according to the present invention. As shown in FIG. 1, the dynamic patella brace 10 includes an elastomeric sleeve 20 and strap assembly 30. Sleeve 20 includes an aperture 21 in which the knee is positioned after the sleeve 20 is drawn up on a user's leg. Strap assembly 30 comprises a central strap portion 31, elastic arm members 17, 18 and 19 extending therefrom, patella bracing pad 15 and anchor 16. Pad 15 is positioned in the inside of the strap assembly, i.e., on the surface adapted to engage the outer surface of sleeve 20. The sleeve 20 is preferably made of an elastomeric material, such as, for example, neoprene rubber. Aperture 21 in sleeve 20 allows for alignment and registration of the knee in the brace when it is positioned therein. The sleeve 20 is also provided with a fastener 12 for anchoring the strap assembly 30 to the sleeve 20 during use. The fastener 12 (shown in FIG. 3) is operatively connected to the anchor 16 of the strap assembly 30 when the brace is in use. The function of the anchor 16 and fastener 12 will be described in more detail below.

The dynamic patella brace 10, according to the present invention, is positioned on the knee between the upper portion and lower portion of the leg of the user (not shown). The elastic arm members 17, 18 of the dynamic patella brace 10 are adapted to be wound circumferentially in a first direction around the knee of the user when the brace is in use. Each of the elastic arm members 17, 18 is attached to the central strap portion 31 on which is disposed the patella bracing pad 15 and arranged so that, when circumferentially wrapped in the first direction about the user's knee when the brace is in use, the bracing pad 15 will cause a resultant force to be applied medially to the user's patella.

Arm members 17 and 18 include thereon fastening and holding means 22 and 23, respectively, which preferably comprise hook-and-loop fastener means, or Velcro® strips attached to the elastic arm members 17, 18 along the outer band surfaces thereof at positions near the points at which the arm members 17, 18 are attached to the patella bracing pad 15. Cooperating fastening and holding means 25, 26 associated respectively with the elastic arm members 17, 18 are attached to the inner band surfaces thereof, respectively, near the ends thereof furthest removed from the point of attachment to the patella bracing pad 15.

Figure 2:
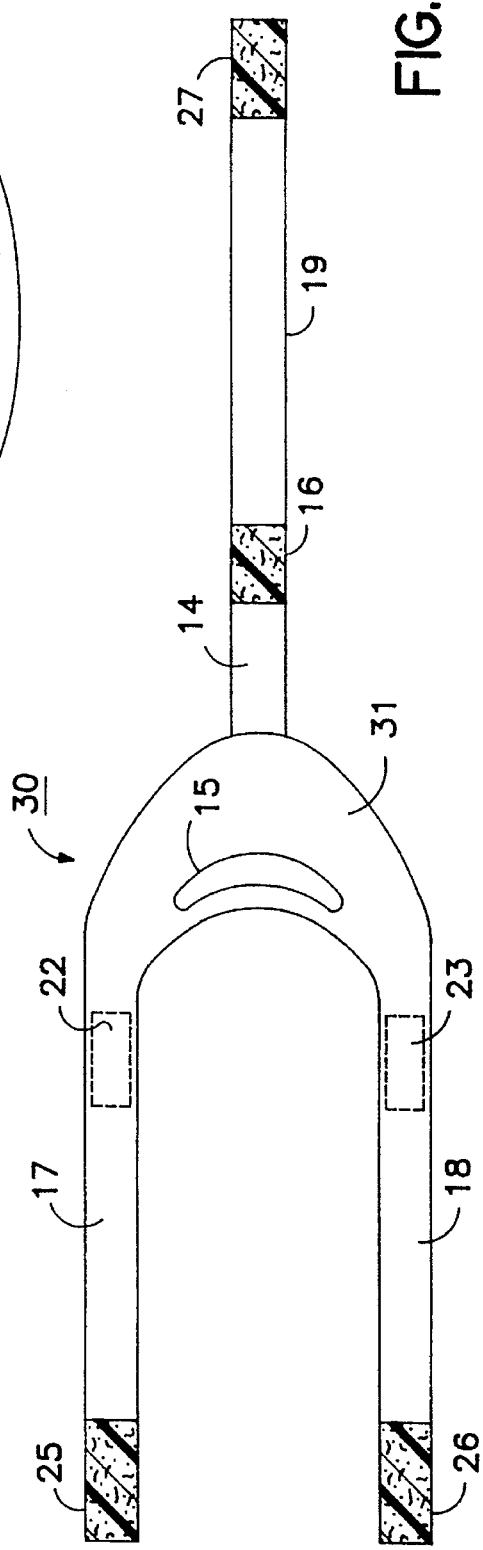
FIG. 2 is a rear view of the strap assembly used to position the patella bracing pad and provide a resultant force to the patella when the brace is in use.

The patella brace 10 also includes a dynamic elastic counterarm 19, having one end thereof also attached to the central strap portion 31 which supports the patella bracing pad 15. The other end of counterarm 19 is adapted to be wrapped circumferentially in a direction opposite to the direction of the first and second elastic arm members 17, 18. A fastening and holding means 27, preferably also a Velcro® strip, is attached to the inner band surface of the elastic arm member 19, as shown in FIG. 2. When the first and second elastic arm members 17, 18 are circumferentially wrapped about the user's knee, they are fastened and held in that position. The fastening means 25 engages with the fastening means 22 on the arm member 17, and the fastening means 26 engages the fastening means 23 on the arm member 18 to hold the arm member 17, 18 in the wrapped position. It is noted that when the right knee of the user is braced, the first arm member 17 is wrapped circumferentially about the knee above the patella, and the second arm member 18 is wrapped circumferentially about the knee below the patella. The opposite arrangement occurs when using the brace on the left knee. These arrangements cause each of the arm members 17, 18 to exert pressure in the medial direction, i.e., toward the center-line of the user, on the patella bracing pad 15 to cause the patella bracing pad 15, positioned laterally of the patella, to thereby apply medial or inwardly directed pressure to the patella, thereby preventing patella subluxation when the knee is flexed.

Additionally, fastening or holding means 29, 30, preferably also Velcro® strips, are attached to the ends of the arm members 17, 18, respectively, at ends thereof furthest removed from the patella bracing pad 15 on the outer band surfaces thereof. These fastening and holding means 29, 30 are adapted to cooperate with the fastening and holding means 27 on the inner surface of the counterarm member 19. When the counterarm member 19 is circumferentially wrapped around the leg of the user with the end thereof furthest from the patella bracing pad 15, fastened and held by cooperation between the fastening means 27 and the fastening means 29, as previously described, it is noted that it would be possible to fasten the end of the counterarm member 19, circumferentially wrapped about the knee by cooperation between the fastening means 27 and the fastening means 30 associated with the lower arm member 18, instead of the fastening means 29, associated with the upper arm member 17. In either case, the counterarm member 19 serves to dynamically stabilize the position of the patella bracing pad on the knee.

In addition, counterarm member 19 includes an elastic portion 14, preferably having substantially greater elasticity than counterarm member 19, disposed adjacent to the anchor 16. The elastic portion 14 is located at a position between the patella bracing pad 15 and the anchor 16. The anchor 16 is adapted to be fastened to the fastener 12, which is positioned on the sleeve 20 as described above. By fixing the anchor 16 to the fastener 12, the two elastic portions 14, 31 of the strap member 30 are allowed to operate in differing manners.

In a preferred embodiment, elastic member 14 is made of a material that is more elastic than that of the strap portion 31 and of the counterarm member 19. By constructing the strap assembly 30 in this manner, the patella bracing pad 15 is permitted to float with the movement of the knee to provide more efficient and stable support to the patella during the entire range of flexion and movement of the knee when the brace is in use, as will be described herein.

In the dynamic patella brace disclosed in my U.S. Pat. No. 4,296,744, the disclosure of which is incorporated herein by reference in its entirety, the patella bracing pad resists adjustment of its position and tends to maintain a more fixed position, regardless of the amount of flexion and movement in the knee when the brace is in use. This results in the patella bracing pad being maintained in a position of lowered effectiveness when the knee of the user is flexed. This is believed to be caused by rigidity of the arm/counterarm assembly when the brace was in use. The brace of U.S. Pat. No. 4,296,744 held the bracing pad in a more fixed position once the elastic arms were engaged, regardless of the stresses placed on the brace as a result of knee flexion by the user. It has been found that this more rigid maintenance of position may cause less efficient stabilization and lowered effectiveness of the brace. To overcome this disadvantage, the subject invention permits the position of the patella bracing pad to be automatically dynamically repositioned based on the amount of flexion and movement of the knee and allows the user to adjust the pressure. Accordingly, the patella bracing pad 15 can be said to float with the flexion and movement of the knee.

To this end, counterarm 19 includes an elastic portion 14, preferably having greater elasticity than counterarm 19. The elastic portion is disposed intermediate the anchor 16 and the pad 15. When the anchor 16 is engaged with the fastener 12 and the knee is flexed, expansion of the sleeve 20 and its aperture 21 will permit the patella bracing pad to dynamically float and align its position with respect to the patella during flexing of the knee. This dynamic repositioning of the pad 15 is possible due to the anchor 16 and fastener 12 arrangement described above, in combination with the elastic portion 14. Fixing the anchor 16 at a predetermined position close to the patella, at a distance preferably in the range of two inches, affords an additional degree of freedom in the lateral direction when the knee is flexed. The anchor 16 placed close to the pad 15 reduces the rigidity of the position maintaining counterarm 19 in the vicinity of the patella, thereby allowing displacement of the pad 15 when the brace is in use. The additional degree of freedom of movement afforded the pad 15 by the positioning of the anchor 16 and fastener 12 allows the pad to dynamically and effectively reposition itself throughout the entire range of flexion and movement of the knee when the brace is in use. To facilitate dynamic positioning of the patella bracing pad 15, the elastic portion 14 of the counterarm 19 is preferably made of a material having greater elasticity than the material of the counterarm member 19. The greater elasticity of the elastic portion 14 of the counterarm member 19 assists in reducing the rigidity of the maintaining structure of the brace when the anchor 16 is engaged with the fastener 12. The anchor 16 permits isolation of the elastic portion 14 of the counterarm member 19 from the strap portion 31 of the assembly 30. Thus, when the knee is flexed, the tendency of the patella bracing pad 15 to be rigidly maintained in position with respect to the patella is avoided by a resultant stretching of the elastic member 14. The patella bracing pad 15 is thus permitted to float and dynamically follows movements of the patella when the knee is flexed.

FIG. 2 shows further details of the strap assembly 30 of the dynamic patella brace 10. As shown, the first and second arm member 17, 18 and the counterarm member 19 are all operatively connected to one another at the central strap portion 31. The patella bracing pad 15 is also attached the central strap portion 31 to which all arm members 17, 18, 19 are attached. The patella bracing pad 15 is preferably attached to the central strap portion 31 by a permanent adhesive. Alternatively, the patella bracing pad 15 may be stitched or otherwise attached to the central strap portion 31. As further shown in FIG. 2, the anchor 16 is made of a material which is fastenable to the fastening area 12 on the sleeve 20. Preferably, this material is made up of a Velcro® strip which would mate with an opposing Velcro® strip 12. Alternatively, the anchor 16 could be a snap, button, or the like, so long as the anchor 16 would function to isolate the elastic portion 14 of the counterarm 19, and be properly fastenable to the fastener 12 when the brace is in use as described above.

In a preferred embodiment, the diameter of the elastic sleeve member 20 and the elastic material and forces thereof are selected so as not to unduly constrict blood flow within the leg or knee of the user. Preferably, a series of different size braces must be provided to accommodate different users. Although a primary purpose of the sleeve 20 and the aperture 21 therein is to permit a relatively unskilled user of the brace to achieve accurate alignment of the patella bracing pad relative to the patella, the elastic sleeve member 20 also inhibits sliding movement of the brace about the knee. However, it is the arrangement, wrapping and fastening of the arm 17, 18, counterarm 19 members and the anchor 16 and fastening means 12 about the knee which primarily cause the patella bracing pad 15 to be maintained in an automatically dynamically repositionable manner laterally of the patella and to cause resultant medially directed pressure thereto throughout the normal range of flexion and movement of the knee by facilitating dynamic repositioning of the patella bracing pad 15 with respect to the patella when the brace is in use.

It should also be noted that the patella bracing pad 15 is arcuately shaped, concave towards the aperture 21 which is adapted to be positioned over the patella when the patella is initially in its normal vertical track defined by the trochlea when the brace is first applied. The bracing pad 15 also preferably has a thickness of elevation to it and is preferably formed from a partially resilient padding material adapted to permit the pad 15 to contour itself to the patella against which it applies the medially directed force. It is also pointed out that the arcuately shaped bracing pad 15, concave towards aperture 21, will tend to dynamically confine the patella to its normal up-and-down movement in the vertical track defined by the trochlea. In particular, during full flexion or bending of the knee, the upper and lower portions of the bracing pad 15 will bend with the knee and will provide pressure surfaces to continuously provide medial pressure against the patella to prevent subluxation in the lateral direction. As previously noted, however, providing an elastic portion 14, isolated by the anchor 16, prevents the tendency of the patella bracing pad 15 to be rigidly maintained in a less effective position with respect to the patella when the knee is flexed and the sleeve 20 and its aperture 21 are thereby expanded. This arrangement provides an additional degree of freedom to the dynamic patella brace which further provides continuous and effective medial pressure against the patella through all flexion and movement of the knee.

In another embodiment, the material used to make up the elastic portion 14 of the counterarm 19 may be made up of the same material as the counterarm 19, so long as the anchor is positioned such that it decreases the rigidity of the counterarm 19 when it is engaged, and in a manner that isolates the elastic portion 14, thereby facilitating automatic dynamic repositioning of the patella bracing pad 15 with respect to the patella when the brace is in use.

It may now be seen that the dynamic patella brace 10 of the present invention may be advantageously used to prevent patella subluxation in the user during all normal degrees of knee flexion and movement. Unlike prior devices, the combination of elastic sleeve 20, circumferentially wrapped arms 17, 18, the circumferentially wrapped counterarm 19 and the isolated elastic portion 14 of the counterarm member 19, isolated by the anchor 16, cause the patella bracing pad 15 to be automatically dynamically repositioned to maintain a more effective and proper position laterally of the patella during all normal degrees of knee flexion and motion and to apply medially directed pressure to the patella of the user to prevent subluxation.

Figure 4:
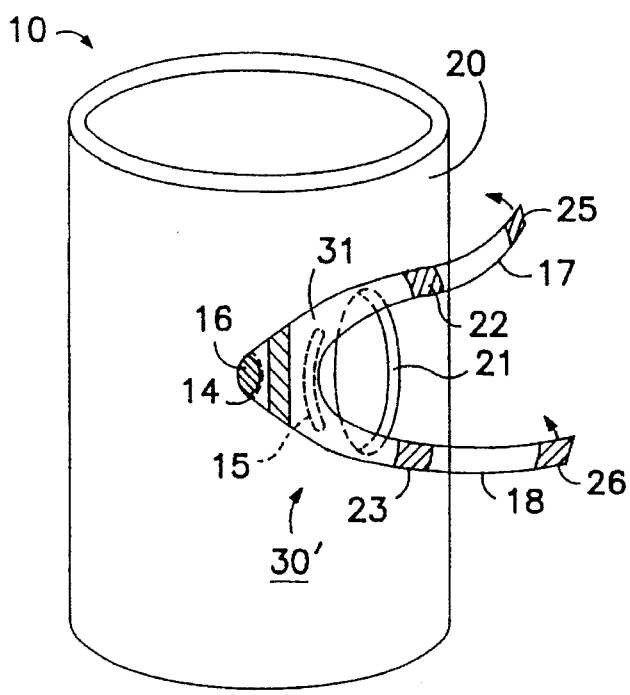
FIG. 4 is a perspective view of an alternate embodiment of the patella brace according to the present invention.
Figure 5:
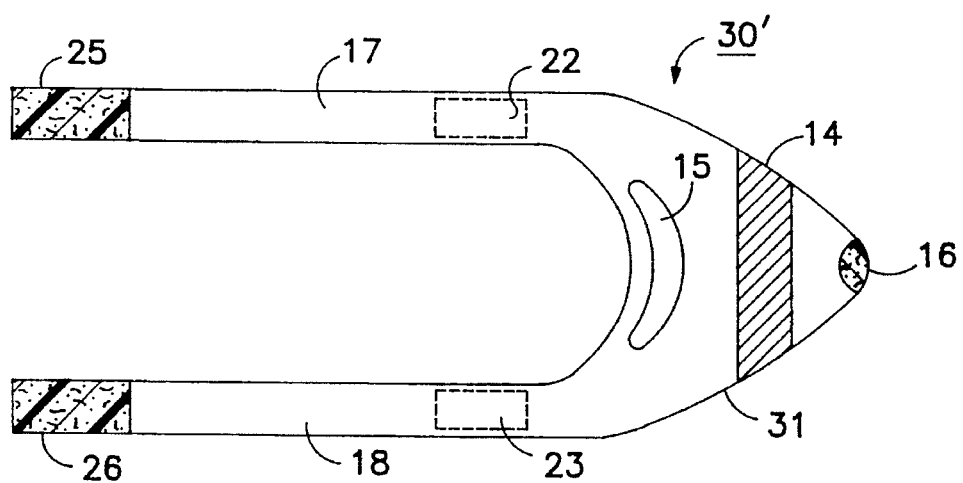
FIG. 5 is a rear view of the strap assembly used to position the patella bracing pad and provide a resultant force to the patella when the brace is in use for the alternate embodiment of the present invention shown in FIG. 4.

In another embodiment of the present invention, as shown in FIGS. 4 and 5, the counterarm member 19 (shown in FIGS. 1 and 2) is removed. In this embodiment, the dynamic patella brace 10 includes an elastomeric sleeve 20 having an aperture 21 in which the knee is positioned during use, and a strap assembly 30' comprising a central strap portion 31, elastic arm members 17 and 18 extending therefrom, patella bracing pad 15 and anchor 16. The sleeve 20, including the aperture 21 and a fastener 12, is substantially identical to that described above with respect to FIGS. 1–3. The dynamic patella brace 10, according to this alternate embodiment of the present invention, is positioned on the knee between the upper portion and lower portion of the leg of the user (not shown). The elastic arm members 17, 18 of the dynamic patella brace 10 are adapted to be wound about the knee of the user when the brace is in use. Each of the elastic arm members 17, 18 extends from the strap assembly 30', on which is disposed the patella bracing pad 15 and arranged so that, when wrapped about the user's knee when the brace is in use, the bracing pad 15 will thereby cause a resultant force to be applied medially to the user's patella. Fastening and holding of the arm members 17, 18 in position is accomplished in the manner described above with respect to FIGS. 1 and 2.

In the alternate embodiment shown in FIGS. 4 and 5, instead of having a counterarm 19 extending from the central strap portion 31, the central strap portion 31 is elongated and the anchor 16 is disposed directly thereon. The central strap portion 31 also includes an elastic strip portion 14 disposed adjacent to the anchor 16 and in between the patella bracing pad 15 and the anchor 16. The anchor is adapted to be fastened to the fastener 12, which is positioned on the sleeve 20 as described above. By fixing the anchor 16 to the fastener 12 and having the elastic strip portion 14 disposed in the central strap portion 31 between the patella bracing pad 15 and the anchor 16, the patella bracing pad 15 is permitted to float with the movement of the knee to provide more efficient and stable support to the patella during the entire range of flexion and movement of the knee when the brace is in use, as described above.

To this end, when the anchor 16 is engaged with the fastener 12 and the knee is flexed, expansion of the sleeve 20 and its aperture 21 will permit the patella bracing pad 15 to dynamically float and align its position with respect to the patella during flexion of the knee by virtue of the above-described construction of the central strap portion 31 including the anchor 16 and the elastic strip portion 14 positioned adjacent the anchor 16.

As described above, fixing the position of the anchor 16 at a predetermined position close to the patella, preferably a distance in the range of two inches from the patella, affords an additional degree of freedom in the lateral direction when the knee is flexed. The anchor 16 placed close to the pad 15 reduces the rigidity of the location of the patella bracing pad 15 in the vicinity of the patella, thereby allowing lateral and medial displacement of the pad 15 when the brace is in use, thus providing closer tracking and control of the patella. The operation of this embodiment of the dynamic patella brace 10 of the present invention is substantially the same as that described above, with the requirement of having a counterarm member being eliminated.

FIG. 5 shows further details of the strap assembly 30'. In this embodiment, the strap assembly 30' comprises a central strap portion 31, elastic arm members 17, 18 extending therefrom, patella bracing pad 15, anchor 16 and elastic strip portion 14 disposed between the patella bracing pad 15 and the anchor 16. Similarly to the strap assembly shown in FIG.

2, the patella bracing pad 15 is preferably attached to the central strap portion 31 by a permanent adhesive. Alternatively, the patella bracing pad 15 may be stitched or otherwise attached to the central strap portion 31. The anchor 16 and fastener 12 arrangement is similar to that described above.

It should also be understood that the anchor 16 and fastener 12 arrangement of the patella brace 10 embodiments described herein may be replaced with an arrangement whereby the anchor 16 is permanently secured to the sleeve 20, such as, for example, by stitching 27 or, alternatively, by a permanent adhesive. Constructing the brace 10 in this manner will not affect the performance of the brace and will result in having a single integrated unit that may be less cumbersome when being put on by the user.

The brace 10 of the invention may also be adapted to be used on either knee of the user. This can be accomplished by providing a fastener in a predetermined location on the sleeve 20 on both sides of the aperture 21 similar to the fastener 12 shown in FIG. 3. By locating a second fastener an equal distance from and opposite of the aperture 21 as the first fastener 12, the sleeve 20 can be used on either the left or right leg of the user since the strap assembly 30 is independent of the sleeve 20.

It is also believed that dynamic patella braces, according to the present invention, are useful for treating patella subluxation by simply preventing further stretching of the ligaments. With repeated subluxation, the media ligament of the patellae (retinaculum) becomes stretched and the lateral ligament (retinaculum) tightens, tending to more readily permit further subluxation occurrences. If the patella brace, according to the present invention, is utilized, however, the patella will be confined to its normal up-and-down, vertical track defined by the trochlea, and, therefore, prevent the development of, or stretch, an already tight lateral retinaculum. Thus, the need for corrective surgery may be avoided. It is also believed that the patella stabilizing brace may be useful in certain forms of isolated patellofemoral chondromalacia by changing opposing contact or pressure points which are frequently painful. Accordingly, it has been seen that the dynamic patella brace, accordingly to the present invention, accomplishes the above-described objectives, as well as other objects which will be apparent to those skilled in the art.

While this invention has been described in conjunction with specific embodiments thereof, it is evident that many alternatives, modifications and variations will be apparent to those skilled in the art. Accordingly, the preferred embodiments of the invention, as set forth herein, are intended to be illustrative, not limiting. Various changes may be made without departing from the true spirit and full scope of the invention, as defined in the following claims.

What is claimed is:

1. A dynamic patella brace, comprising:
   a patella bracing strap including an anchor, a patella bracing pad and first and second arm members extending from said strap, first ends of said first and second arm members being adapted to be wrapped about a knee of a user to apply a dynamic resultant force in the medial direction to the patella via the patella bracing pad throughout the complete functional physiologic range of flexion and movement of the knee when the brace is in use;
   said anchor being disposed a sufficient distance laterally adjacent said patella bracing pad so as to maintain the patella bracing pad positioned laterally adjacent to the patella throughout the complete functional physiologic range of flexion and movement of the knee when the brace is in use;
   said strap further including an intermediate portion disposed between the anchor and the patella bracing pad, said intermediate portion being of sufficient length to allow said patella bracing pad to float with movement of the knee and to be dynamically repositioned depending upon the amount of flexion and movement of the knee when the brace is in use; and
   an elastomeric sleeve having an aperture, said sleeve being adapted to have the knee positioned substantially within the aperture, and further including a first fastener positioned at a first predetermined location on said sleeve for enabling said anchor to be attached to said sleeve when the brace is in use.

2. The dynamic patella brace of claim 1, wherein said intermediate elastic member has an elasticity greater than that of said patella bracing strap.

3. The dynamic patella brace of claim 1, wherein said patella bracing pad is arcuately shaped, having a concave portion thereof adapted to face toward the patella when the brace is in use.

4. The dynamic patella brace of claim 1, wherein said first and second arm members are adapted to be wrapped about the knee above and below the patella when the brace is in use.

5. The dynamic patella brace of claim 3, wherein said first and second arm members are adapted to be wrapped about the knee above and below the patella when the brace is in use.

6. The dynamic patella brace of claim 4, wherein said first and second arm members and said anchor further comprise fasteners adapted to hold ends thereof in place to prevent the unwrapping and unfastening of said members when the brace is in use.

7. The dynamic patella brace of claim 2, wherein said intermediate portion has an elasticity greater than that of said patella bracing strap.

8. The dynamic patella brace of claim 1, wherein the sleeve is adapted to be worn on either knee of a user and further comprises a second fastener positioned at a second predetermined location on said sleeve.

9. The dynamic patella brace of claim 1, wherein said anchor and said first fastener are adapted to form an integral unit, said integral unit being permanently fixed to said sleeve at said first predetermined position.

10. The dynamic patella brace of claim 9, wherein said integral unit is stitched to said sleeve.

11. The dynamic patella brace of claim 9, wherein said integral unit is glued to said sleeve.

12. A dynamic patella brace comprising:
    a patella bracing strap including a patella bracing pad, an anchor and first and second arm members extending from said strap, first ends of said first and second arm members being adapted to be wrapped about the knee in a first direction to apply a resultant force, via the patella bracing pad, to the patella in the medial direction throughout the complete functional physiologic range of flexion and movement of the knee when the brace is in use;
    a third arm member extending from said strap, a first end of said third arm being adapted to be wrapped about the knee in a second direction, said second direction being opposite that of said first direction, said third arm including an anchor between an elastic portion of said third arm and said first end, said anchor being spaced a sufficient distance laterally adjacent said patella bracing pad for maintaining said patella bracing pad positioned laterally of the patella throughout the complete functional physiologic range of flexion and movement when the brace is in use, said elastic portion being positioned between said anchor and said patella bracing pad adjacent said patella bracing pad and being adapted to cooperate with the anchor to permit the patella bracing pad to be automatically dynamically repositioned based on the amount of flexion and movement of the knee; and an elastic sleeve adapted to have the knee positioned substantially within said sleeve and adapted to receive the anchor for fastening of the anchor to the sleeve, including a first fastener attached to said sleeve at a first predetermined position when the brace is in use.

13. The dynamic patella brace of claim 12, wherein the elastic portion of the third arm has an elasticity greater than that of the first portion of the third arm.

14. The dynamic patella brace of claim 12, wherein the patella bracing pad is arcuately shaped, having a concave portion thereof adapted to face toward the patella when the brace is in use.

15. The dynamic patella brace of claim 13, wherein the patella bracing pad is arcuately shaped, having a concave portion thereof adapted to face toward the patella when the brace is in use.

16. The dynamic patella brace of claim 13, wherein the first and second arm members are adapted to be wrapped about the knee above and below the patella when the brace is in use.

17. The dynamic patella brace of claim 13, wherein said first, second and third arm members further comprise fasteners adapted to hold ends thereof in place to prevent the unwrapping of said members when the brace is in use.

18. The dynamic patella brace of claim 16, wherein said first, second and third arm members further comprise fasteners adapted to hold ends thereof in place to prevent the unwrapping of said members when the brace is in use and said elastic portion comprises an elastic strip.

19. The dynamic patella brace of claim 13, wherein the sleeve is adapted to be worn on either knee of a user, and further comprises a second fastener positioned at a second predetermined location on said sleeve.

20. An improved dynamic patella brace, comprising:

a patella bracing strap including an anchor, a patella bracing pad thereon and first and second freely extending arm members extending from said strap;

said anchor being lateral of and spaced from said patella bracing pad by;

said patella bracing strap further including an intermediate portion disposed between the anchor and the patella bracing pad; and said anchor being spaced from said patella pad a sufficient distance to allow said patella pad to float with movement of the knee; and an elastomeric sleeve having an aperture, and further including a first fastener positioned at a first predetermined location on said sleeve for enabling said anchor to be attached to said sleeve.

21. The dynamic patella brace of claim 20, wherein said intermediate portion has an elasticity greater than that of said patella bracing strap.

22. The dynamic patella brace of claim 21, wherein said patella bracing pad is arcuately shaped, having a concave portion thereof adapted to face toward the patella when the brace is in use and said intermediate portion comprises an elastic strip.

23. In a dynamic patella brace having an elastomeric sleeve with an aperture adapted to expose the knee, and a patella bracing pad for applying medial pressure to the patella, the improvement comprising means for freely floatingly mounting said patella bracing pad on said sleeve laterally of said aperture so that said patella bracing pad moves relative to said sleeve in vertical directions and automatically tracks vertical movement of said patella throughout the functional physiological range of flexion and movement of the knee while applying said medial pressure to said patella.

24. The dynamic patella brace defined in claim 23 wherein said means for floatingly mounting said patella bracing pad on said sleeve includes a patella bracing strap and anchor means, first and second arm members extending from said strap, first ends of said first and second arm members being adapted to be wrapped about a knee of a user to apply a dynamic resultant force in the medial direction to the patella via the patella bracing pad, said anchor being positioned a sufficient distance laterally adjacent said patella bracing pad so as to maintain the patella bracing pad positioned laterally adjacent to said patella throughout the complete functional physiologic range of flexion and movement of the knee when the brace is in use.

25. The dynamic patella brace defined in claim 24 including an intermediate elastic member disposed between said anchor means and the patella bracing pad, said intermediate elastic member being of sufficient length to allow said patella bracing pad to float with movement of the knee and to be dynamically repositioned depending upon the amount of flexion and movement of the knee when the brace is in use.

26. The dynamic patella brace defined in claim 25, wherein said intermediate elastic member has an elasticity greater than that of said patella bracing strap.

27. The dynamic patella brace defined in claim 25, wherein said first and second arm members are adapted to be wrapped about the knee above and below the patella when the brace is in use.

28. The dynamic patella brace defined in claim 24, wherein the strap is made of an elastomeric material.

29. The dynamic patella brace defined in claim 24, wherein said anchor means and said first fastener are adapted to form an integral unit.

30. A method of dynamically stabilizing the patella of a human knee during flexion movement comprising:

a) enveloping said human knee with a compressive elastomeric sleeve having an aperture adapted to minimize compressive pressure on the patella.

b) mounting a patella bracing pad on said sleeve so that said bracing pad freely floats relative to said compressive elastomeric sleeve and automatically tracks vertical movement of said patella throughout the functional physical range of flexion and movement of said knee while applying medial pressure to said patella.

31. A method dynamically stabilizing the patella of a human knee for diagnosis and treatment of patella subluxation during flexion movement comprising:

a) enveloping said human knee with a compressive elastomeric sleeve having an aperture adapted to minimize compressive pressure on the patella b) applying medial pressure to said patella via a bracing pad freely mounted on said sleeve along a path automatically tracking vertical movement of said patella throughout the functional physiological range of flexion and movement of said knee.

\* \* \* \* \*